(12) United States Patent
Woudenberg et al.

(10) Patent No.: US 6,414,206 B2
(45) Date of Patent: Jul. 2, 2002

(54) PROCESS FOR PREPARING BISINDENYLALKANES

(75) Inventors: Richard Herman Woudenberg, Elst; Faysal Kalmoua, Oss, both of (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/790,823

(22) Filed: Feb. 22, 2001

(30) Foreign Application Priority Data

Feb. 23, 2000 (GB) ............................................. 00200628

(51) Int. Cl.⁷ ............................. C07C 1/26; C07C 2/76; C07C 13/28; C07C 15/24
(52) U.S. Cl. ....................... 585/360; 585/359; 585/431; 585/438; 585/469
(58) Field of Search ................................ 585/359, 360, 585/431, 438, 469

(56) References Cited

U.S. PATENT DOCUMENTS 5,145,819 A    9/1992   Winter et al. ................ 502/117

FOREIGN PATENT DOCUMENTS

| EP | 0 485 823 | 5/1992 |
| EP | 0 574 597 | 12/1993 |
| EP | 0 575 875 | 12/1993 |

OTHER PUBLICATIONS

*Journal of Organometallic Chemistry*, X–Ray structures of ethylenebis (tetrahydroindenyl)–titanium and –zirconium dichlorides: a revision, Scott Collins, et al., pp. 21–29.
*J. American Chemical Society 1987*, pp. 6544–6545, and 18 pages Supplementary Material mentioned at p. 6545.
*American Chemical Society—Organometallics 1991*,—Syntheses of [Ethylene–1,2–bis(n⁵–4,5,6, 7–tetrahydro–1–Indenyl)]zirconium and –hafnium Hydride Complexes. Improved Syntheses of the Corresponding Dichlorides, Robert B. Grossman, et al., pp. 1501–1505.
*Advanced Organic Chemistry*, Reactions, Mechanisms, and Structure, Fourth Edition—Aliphatic Nucleophilic Substitution—The Effect of the Leaving Group, pp. 352–357.
*Advanced Organic Chemistry*, Reactions, Mechanisms, and Structure, Fourth Edition—Aliphatic Nucleophilic Substitution—Metal Electrophiles, pp. 606–609.

European Search Report EP 00 20 0628.

*Primary Examiner*—Thuan D. Dang
(74) *Attorney, Agent, or Firm*—Richard P. Fennelly

(57) ABSTRACT

The present invention relates to a process for preparing bisindenylalkanes of formula I:

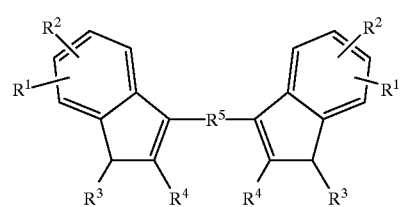

I wherein $R^1$, $R^2$, $R^3$, and $R^4$ independently represent H or a $C_1$–$C_6$ hydrocarbon group or $R^1$ and $R^2$ or $R^1$ and $R^3$ or $R^3$ and $R^4$ together with the carbon atoms to which they are attached form a saturated or unsaturated 5- or 6-membered ring, said ring being optionally substituted with a $C_1$–$C_4$ hydrocarbon group, and $R^5$ represents a $C_1$–$C_6$ hydrocarbon group, comprising reacting, at a temperature which does not exceed about 5° C., a metallated indene of formula II with a disubstituted hydrocarbon of formula III:

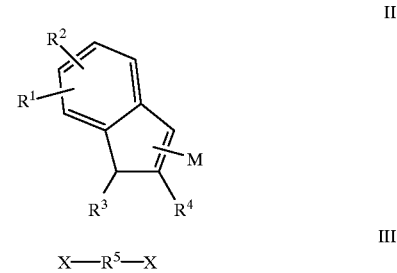

II

III wherein $R^1$, $R^2$, $R^3$, $R^4$, and $R^5$ have the same meaning as defined above, M represents a metal ion, and X independently represents a suitable leaving group, in a suitable reaction medium wherein the molar ratio of II to III is 2.05 or higher. The process is particularly suitable for preparing bisindenylethane, i.e., $R^1$–$R^4$ represent H and $R^5$ represents an ethylene group.

12 Claims, No Drawings

PROCESS FOR PREPARING BISINDENYLALKANES

This application claims priority from European Patent Application No. 00200628.6, filed Feb. 23, 2000.

The present invention relates to a process for preparing bisindenylalkanes, in particular bisindenylethane and analogues thereof.

Bisindenylethane, i.e. 1,2-bis(3-indenyl)ethane, is an intermediate in the synthesis of metallocene catalysts which typically are used in combination with a co-catalyst such as methylaluminoxane for the isospecific (co)polymerization of ethylenically unsaturated monomers, e.g., the production of isotactic polypropylene.

Several processes for preparing bisindenylethane and analogues thereof are known in the art.

*J. Organometallic Chemistry*, 342 (1988) 21–29, to S. Collins et al. discloses a process for preparing 1,2-bis(3-indenyl)ethane from 1,2-dibromoethane wherein two (see page 22, Scheme 1) or less than two equivalents (see page 27, Example 1) of indenyllithium are used. The reaction was carried out in solution in THF/HMPA and by slowly warming the reaction mixture from −78° C. to room temperature and gave the desired end-product in 65% yield after crystallization from acetone and ethanol.

*J. Am. Chem. Soc.*, 109 (1987) 6544–6545, to J. A. Ewen et al. discloses a process similar to the one of Collins wherein, as described in the supplementary material to the article, two equivalents of indenyllithium are reacted with 1,2-dibromoethane dissolved in THF by warming the reaction mixture from −91° C. to 25° C. and stirring for 4 h. Bisindenylethane was obtained in a crude yield of 60%. The product was recrystallized from ethanol.

EP-A-0 485 823 to Hoechst discloses a process similar to that of Collins, but with the modification that the reaction is performed in a solution of just THF. Bis(2-methyl-indenyl) ethane was obtained after warming the reaction mixture from −78° C. to room temperature and stirring for 5 h in 49% yield after chromatographic purification (see page 9, Example III).

EP-A-0 575 875 to Spherilene discloses a process similar to the Hoechst one; however, the reaction mixture is warmed from −78° C. to 50° C. and the reaction mixture is stirred for 12 h. A yield of 51.6% of unpurified bisindenylethane was obtained (see page 8, lines 44–57). A yield of 48% of crude product was obtained when 4,7-dimethylindene was one of the starting materials (see page 9, line 53, through page 10, line 4).

*Organometallics*, 10 (1991) 1501–1505, to Grossman et al. discloses the preparation of 1,2-bis(3-indenyl)ethane on page 1502 (left column) in a yield of 54% (crude) by reacting indenyllithium with 1,2-dibromoethane in a molar ratio of 2.2:1 at −78° C., warming the solution to room temperature, and stirring for several hours at this temperature.

As an alternative to the homogeneous processes described above, EP-A-0 574 597 to Hoechst discloses the preparation of bisindenyl compounds of a formula III via a heterogeneous reaction (i.e. suspension) in an aliphatic or aromatic hydrocarbon. The reaction scheme on page 4 of this document gives a general description of the synthesis of bisindenyl compounds (the preparation of bisindenylethane is neither described nor exemplified in this document). The reaction conditions are mentioned on page 8 of this document. In particular, it is mentioned in line 48 of page 8 that the reaction temperature preferably is from 0 to 120° C. and in line 53 that the molar ratio of metallated indene to inter alia dibromoalkyl compound preferably is 2:1.

These prior art processes have the disadvantage that the yields are low (we found that the main by-product is spiro-indene in the case of bisindenylethane) and that as a result thereof the bisindenylalkane needs to be purified—in particular, chromatographic purification is undesired when the reaction is carried out on an industrial scale—before further reaction (toward a metallocene catalyst) can take place. In some cases, the reaction times are unacceptably long as well. We have found a new process which does not suffer from these drawbacks.

According to the present invention, a process is provided for preparing bisindenylalkanes of formula I:

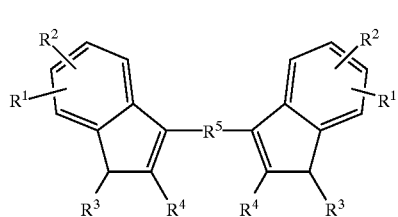

I wherein $R^1$, $R^2$, $R^3$, and $R^4$ independently represent H or a $C_1$–$C_6$ hydrocarbon group or $R^1$ and $R^2$ or $R^1$ and $R^3$ or $R^3$ and $R^4$ together with the carbon atoms to which they are attached form a saturated or unsaturated 5- or 6-membered ring, said ring being optionally substituted with a $C_1$–$C_4$ hydrocarbon group, and $R^5$ represents a $C_1$–$C_6$ hydrocarbon group, comprising reacting, at a temperature which does not exceed about 5° C., a metallated indene of formula II with a disubstituted hydrocarbon of formula III:

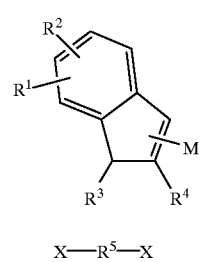

II

X—$R^5$—X

III wherein $R^1$, $R^2$, $R^3$, $R^4$, and $R^5$ have the same meaning as defined above, M represents a metal ion, and X independently represents a suitable leaving group, in a suitable reaction medium wherein the molar ratio of II to III is 2.05 or higher.

Hence, the molar ratio of II to III is 2.05:1 or higher. Preferably, the molar ratio of metallated indene (II) to disubstituted hydrocarbon (III) is 2.1 or higher, more preferably 2.2 or higher, most preferably 2.2 to 3.0.

At temperatures above about 5° C. by-products are being formed at an undesirable level. Hence, preferably the reaction temperature does not exceed about 0° C.

It was found that when using a reaction temperature and a molar ratio of metallated indene to disubstituted hydrocarbon as presently claimed, the product selectivity, reaction time and/or yield improved considerably over the values described in the prior art.

$R^1$, $R^2$, $R^3$, and $R^4$ independently represent H or a $C_1$–$C_6$ hydrocarbon group or $R^1$ and $R^2$ or $R^1$ and $R^3$ or $R^3$ and $R^4$ together with the carbon atoms to which they are attached form a saturated or unsaturated 5- or 6-membered ring, said ring being optionally substituted with a $C_1$–$C_4$ hydrocarbon group. It is noted that in the case that $R^3$ and $R^4$ together with the carbon atoms to which they are attached form an aromatic ring, the double bond in the five-membered ring in the compound of formula I and II will shift to the position of the carbon atoms to which $R^3$ and $R^4$ are attached as, for example, when fluorene is used as a starting material (see below). Preferably, $R^1$, $R^2$, $R^3$, and $R^4$ independently represent H or a $CH_3$ (i.e. methyl) group, most preferably H.

Typical examples of indenes from which the metallated indene of formula II can be prepared include indene, 2-methylindene, 2-methylbenzoindene, 4,7-dimethylindene, and fluorene. These starting materials are either commercially available or can be prepared by methods known to a person skilled in this art, e.g., see page 8, lines 11–36, of EP-A-0 574 597 cited above.

$R^5$ represents a $C_1$–$C_6$ hydrocarbon group. It may be a linear or branched, divalent hydrocarbon group. Preferably, it represents a linear $C_2$–$C_4$ hydrocarbon group. Most preferably, it represents an ethylene group.

M represents a metal ion. Suitable metal ions include alkali and alkaline-earth metal ions such as Li, Na, K, and Mg. Most preferably, M represents a Li ion.

X independently represents a suitable leaving group. Such groups are known to a person skilled in this art, for example, the ones discussed on pages 352–357 of J. March, *Advanced Organic Chemistry*, Fourth Edition, John Wiley & Sons, New York, 1992. Suitable leaving groups include halogen atoms and mesylate, tosylate, and triflate groups. Preferably, the leaving group is a halogen atom such as a Br or Cl atom. More preferably, X represents a Br atom. Most preferably, each X represents a halogen atom, in particular a Br atom.

A typical example of a compound according to formula III is 1,2-dibromoethane. Compounds of formula III are either commercially available or can be prepared by methods known per se in the art.

The metallated indene of formula II is prepared according to procedures known to a skilled person. Suitable metallating agents or bases are known and are described, for example, in J. March, *Advanced Organic Chemistry*, Fourth Edition, pages 606–609. Typical examples include n-butyllithium, sodium hydride, potassium hydride, lithium diisopropylamide, sodium amide, potassium amide, alkyl magnesium halides, and dialkyl magnesium compounds with n-butyllithium being preferred. Typically, the metallating agent is used in the form of a solution or dispersion in a suitable solvent such as hexane or THF.

The invention process can be carried out using means and equipment well-known to a person skilled in this art.

The invention process is carried out in a reaction medium suitable for carrying out the metallation and claimed alkylation reactions. Suitable reaction media are known to the skilled person and typically include alkanes such as hexane, heptane, and toluene, and ethers such as diethyl ether and tetrahydrofuran (THF), with ethers being preferred. Mixtures of one or more of these media may also be used. Most preferably, the reaction medium of the invention process comprises THF. Preferably, a minimal amount of the reaction medium is used in the process according to the present invention.

The invention process is particularly suitable for preparing bisindenylethane, i.e., $R^1$–$R^4$ represent H and $R^5$ represents an ethylene group. This product is prepared from indene and a 1,2-dihaloethane, preferably 1,2-dibromoethane.

The metallated indene of formula II can be prepared in a wide temperature range, i.e., typically −100° C. to room temperature. After addition of the metallating agent to the indene, the reaction mixture may be warmed to room temperature in order to form the metallated indene of formula II within an acceptable reaction time. A practical temperature for carrying out the metallation reaction on a small scale is at about −78° C. On a technical scale, working at such low temperatures is expensive, and it was found that the reaction could be conveniently carried out at a temperature of about −15° C.

A typical reaction time for the invention process is 4 to 5 hours. Typically, the reaction time decreases with an increasing molar ratio of II to III.

It is to be noted that, depending on the concentration, reaction medium, and temperature, the reaction mixture of, e.g., indenyllithium and 1,2-dibromoethane in THF may be a heterogeneous mixture below a certain temperature, whereas above this temperature it may be a homogeneous mixture.

The present invention is illustrated by the following Examples.

EXAMPLES 1–7 AND COMPARATIVE EXAMPLE A

Typical procedure for the preparation of bisindenylethane

Stoichiometric quantities of indene and n-butyllithium (e.g. 2.5 M in hexane) were reacted at −78° C. in a suitable solvent (e.g. THF) and in a suitable reaction vessel. After stirring the reaction mixture for half an hour at this temperature, 1,2-dibromoethane was added in an amount as claimed. The reaction mixture was then allowed to warm up to 0° C. and was stirred for typically 4 to 5 hours. Addition of water, followed by evaporation of the organic solvents yielded a crude product, which was washed several times with ethanol. Recrystallization from ethanol/toluene produced bisindenylethane in a good yield and high purity. Table I lists the data for a number of typical experiments using 75 mmoles of indene.

TABLE I

Preparation of bisindenylethane

| Example | Molar ratio[1] | Selectivity[2] | Reaction time[3] | Yield[4] |
| --- | --- | --- | --- | --- |
| A | 2.0 | 85:15 | 36 | 48 |
| 1 | 2.05 | 85:15 | 18 | 61 |
| 2 | 2.1 | 88:12 | 15 | 70 |
| 3 | 2.2 | 93:7 | 5 | 80 |
| 4 | 2.3 | 93:7 | 5 | 80 |
| 5 | 2.5 | 94:6 | 4 | 83 |
| 6 | 2.7 | 95:5 | 4 | 85 |
| 7 | 3.0 | 95:5 | 4 | 85 |

[1]Molar ratio is the ratio of indenyllithium to 1,2-dibromoethane
[2]Selectivity is the ratio of bisindenylethane to by-products (mainly spiroindene) as determined by $^1$H-NMR
[3]Reaction time is expressed in hours
[4]Isolated yield The data in Table I illustrates that when using the process according to the present invention (i.e. Examples 1–7), bisindenylethane was obtained in a shorter reaction time, with an equal or better selectivity, and in a higher chemical yield than when using any of the processes described in the prior art. Comparative Example A shows that in order to obtain these beneficial effects, the temperature as well as the molar ratio requirements defined in claim 1 should be met.

What is claimed is:

1. A process for preparing bisindenylalkanes of formula I:

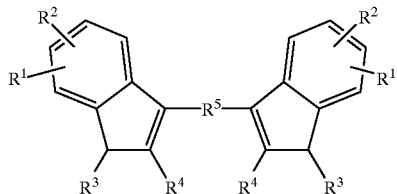

wherein $R^1$, $R^2$, $R^3$, and $R^4$ independently represent H or a $C_1$–$C_6$ hydrocarbon group or $R^1$ and $R^2$ or $R^1$ and $R^3$ or $R^3$ and $R^4$ together with the carbon atoms to which they are attached form a saturated or unsaturated 5- or 6-membered ring, said ring being optionally substituted with a $C_1$–$C_4$ hydrocarbon group, and $R^5$ represents a $C_1$–$C_6$ hydrocarbon group, comprising reacting, at a temperature which does not exceed about 5° C., a metallated indene of formula II with a disubstituted hydrocarbon of formula III:

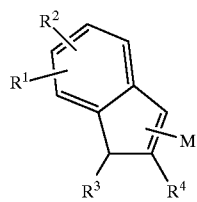

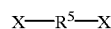

wherein $R^1$, $R^2$, $R^3$, $R^4$, and $R^5$ have the same meaning as defined above, M represents a metal ion, and X independently represents a suitable leaving group, in a reaction medium wherein the molar ratio of II to III is 2.05 or higher.

2. A process according to claim 1, characterized in that the molar ratio is 2.1 or higher.

3. A process according to claim 1 or 2, characterized in that the molar ratio is 2.2 or higher.

4. A process according to claim 1 or 2, characterized in that the reaction temperature does not exceed about 0° C.

5. A process according to claim 1 or 2, characterized in that $R^1$, $R^2$, $R^3$, and $R^4$ independently represent H or a $CH_3$ group.

6. A process according to claim 1 or 2, characterized in that $R^5$ represents a linear $C_2$–$C_4$ hydrocarbon group.

7. A process according to claim 1 or 2, characterized in that M represents an alkali or alkaline-earth metal ion.

8. A process according to claim 1 or 2, characterized in that X independently represents a halogen atom.

9. A process according to claim 1 or 2, characterized in that the reaction is carried out in an alkane or ether reaction medium.

10. A process according to claim 9, characterized in that the reaction medium comprises tetrahydrofuran.

11. A process according to claim 1 or 2, characterized in that M represents a Li ion.

12. A process according to claim 1 or 2, characterized in that X independently represents a Br atom.

* * * * *